United States Patent [19]

Hanson et al.

[11] Patent Number: 5,441,887

[45] Date of Patent: Aug. 15, 1995

[54] RAPID DEGRADATION OF HALOGENATED HYDROCARBONS BY SOLUBLE METHANE MONOOXYGENASE

[75] Inventors: Richard S. Hanson; John D. Lipscomb, both of Wayzata, Minn.; Brian G. Fox, Madison, Wis.

[73] Assignees: Regents of the University of Minnesota, Minneapolis; BioTrol, Inc., Eden Prairie, both of Minn.

[21] Appl. No.: 235,193

[22] Filed: Apr. 29, 1994

Related U.S. Application Data

[60] Continuation of Ser. No. 886,608, May 20, 1992, abandoned, which is a division of Ser. No. 814,202, Dec. 20, 1991, Pat. No. 5,196,339, which is a continuation of Ser. No. 384,859, Jul. 21, 1989, abandoned, which is a continuation of Ser. No. 272,538, Nov. 17, 1988, abandoned.

[51] Int. Cl.$^6$ .................... C12S 13/00; B09B 3/00; C12N 1/30; C02F 3/00
[52] U.S. Cl. ................... 435/262.5; 435/262; 435/250; 435/155; 435/189; 210/606
[58] Field of Search ............ 435/262, 262.5, 252.1, 435/248, 249, 250, 157, 156, 189, 155; 210/606, 610, 611

[56] References Cited

U.S. PATENT DOCUMENTS

| | | | |
|---|---|---|---|
| 4,323,649 | 4/1982 | Higgins | 435/156 |
| 4,493,895 | 1/1985 | Colanuotolo et al. | 435/262 |
| 4,587,216 | 5/1986 | Patel et al. | 435/156 |
| 4,594,324 | 6/1986 | Dalton et al. | 435/156 |
| 4,713,343 | 12/1987 | Wilson, Jr. et al. | 435/262 |

(List continued on next page.)

FOREIGN PATENT DOCUMENTS 0289350 11/1988 European Pat. Off. .

OTHER PUBLICATIONS

Colby et al. "Resolution of the Methane Mono-oxygenase of *M. capsulatae* (Bath) into Three Components", *Biochem. J.* vol. 171 (1978) pp. 461–468.

Pilkington et al. "Purification and Characterisation of the Soluble Methane monooxygenase from *M. Sporium*", *FEMS Microbiology Letters*, vol. 78 (1991) pp. 103–108.

Egli et al., "Anaerobic dechlorination of tetrachlorination of tetrachloromethane", *FEMS Microbiology Letters*, vol. 43 (1987) pp. 257–261.

Nelson et al. "Aerobic Metabolism of TCE by a Bacterial Isolate", *Appld. and Environmental Micro.* (Aug., 1986) pp. 383–384.

Fox et al. "Complex Formation between the Protein Components of Methane Monooxygenase from *Methylosinus trichosporium* OB3b" *J. Bio Chem.* vol. 266 No. 1 (Jan. 1991) pp. 540–550.

Mossbauer et al. "Evidence for a M-Oxo-bridged Binclear Iron Cluster" vol. 263 No. 22 (Aug. 1988) pp. 10553–6.

Nakajima et al. "Purification Properties of Soluble Methane Monooxygenase" *Biosci Biotech Biochem* vol. 56 No. 5 (1992) pp. 736–740.

J. T. Wilson et al., *Appl. Environ. Microbiol.*, 49, 242 (1985).

(List continued on next page.)

*Primary Examiner*—Michael G. Wityshyn
*Assistant Examiner*—T. J. Reardon
*Attorney, Agent, or Firm*—Merchant, Gould, Smith, Edell, Welter & Schmidt

[57] ABSTRACT

A method is disclosed for degradation of a halogenated hydrocarbon compound such as trichloroethylene (TCE) which utilizes a soluble methane monooxygenase or a bacterium comprising the monooxygenase. *Methylosinus trichosporium* OB3b is a soluble methane monooxygenase-producing bacterium which when cultivated by continuous culturing comprising exposing the bacterium to a continuous-flow gas mixture of air and methane in a ratio of about 25:1–1:20, respectively. *Methylosinus trichosporium* OB3b is capable of degrading TCE at rates from about 500–10,000 micromoles per hour per gram cells. The present method is useful to degrade halogenated hydrocarbon compounds such as TCE at initial concentrations up to 10,000 micromoles/l.

7 Claims, 5 Drawing Sheets

U.S. PATENT DOCUMENTS

| | | | |
|---|---|---|---|
| 5,013,665 | 5/1991 | Suzuki et al. | 435/252.1 |
| 5,190,870 | 3/1993 | Lipscomb et al. | 435/155 |
| 5,192,672 | 3/1993 | Lipscomb | 435/155 |
| 5,196,339 | 3/1993 | Hanson et al. | 435/262 |
| 5,316,940 | 5/1994 | Geongiou et al. | 435/252.1 |

OTHER PUBLICATIONS

E. J. Bouwer et al., *Appl. Environ. Microbiol.*, 45, 1286 (1983).
C. Egli et al., *FEMS Microbiol. Letter*, 43, 257 (1987).
I. J. Higgins et al., *Nature*, 286, 561 (1980).
C. L. Haber et al., *Science*, 221, 1147 (1983).
M. M. Fogel et al., *Appl. Environ. Microbiol.*, 51, 720 (1986).
K. J. Burrows et al., *J. Gen. Microbiol.*, 130, 3327 (1984).
B. G. Fox et al., *Biochem. and Biophys. Res. Comm.*, 154, 165 (1988).
M. J. K. Nelson et al., *Appl. Environ. Microbiol.*, 54, 604 (1988).
M. J. K. Nelson et al., *Appl. Environ. Microbiol.*, 52, 383 (1986).
R. Whittenbury et al., *J. Gen. Microbiol.*, 61, 205 (1970).
A. Cornish, *J. Gen. Microbiol.*, 130, 2565 (1984).
T. E. Patt et al., *Int. J. Systematic Bacteriol.*, 26, 226 (1976).
G. M. Tonge et al., *FEBS Letters*, 58, 293 (1975).
D. I. Stirling et al., *Eur. J. Biochem.*, 96, 205 (1979).
D. I. Stirling et al., *Biochem. J.*, 177, 361 (1979).
J. Baschnagel-DePamphillis et al., *J. Bacteriol.*, 98, 222 (1969).
H. Dalton et al., "Physiology and Biochemistry of Methylotrophic Bacteria" in *Microbiological Growth on One-Carbon Compounds*; S. Hegedous, R. Hansen, and D. Kurz, Eds.; Martinus Nijhoff Publishers; Dodrecht, pp. 89–94.
J. Green et al., *J. Biolog. Chem.*, 260, 15795 (1985).
M. J. K. Nelson et al., *Appl. Environ. Microbiol.*, 53, 949 (1987).
R. N. Patel et al., *J. Bacteriol.*, 169, 2313 (1987).
D. Scott et al., *J. Gen Microbiol.*, 125, 63 (1981).
G. M. Tonge et al., *Biochem. J.*, 161, 333 (1977).
T. E. Patt et al., *J. Bacteriol.*, 120, 955 (1974).
L. P. Wackett et al., *Appl. and Environ. Microbiol.*, 54, 1703 (1988).
J. Green et al., *Eur. J. Biochem.*, 153, 137–144 (1985).
J. Green and H. Dalton, *Biochem. J.*, 236, 155–162 (1986).
T. Imai et al., *Appl. Environ. Microbiol.*, 52, 1403–1406 (1986).
J. Lund et al., *Eur. J. Biochem.*, 147, 297–305 (1985).
J. Lund and H. Dalton, *Eur. J. Biochem*, 147 291–296 (1985).
R. N. Patel, *Arch. Biochem. Biophys.*, 252, 229–236 (1987).
S. D. Prior and H. Dalton, *J. Gen. Microbiol.*, 131, 155–163 (1985).
I. G. Sokolov et al., *Microbiology*, 53, 733–739 (1984).
D. I. Sterling and H. Dalton, *FEMS Microbiol. Let.*, 5, 315–318 (1979).
M. P. Woodland and H. Dalton, *Anal. Biochem.*, 139, 459–462 (1984).
Joergensen et al–Chem. Abst. vol. 100 (1984) p. 48315S.
Higgins–Chem. Abst. vol. 96 (1982) p. 197913m.
Little et al., *App. Enviro. Microbiol.*, 54:951–956 (1988).
Miller et al., *Biochemistry*, 21:1090–1097 (1982).

RAPID DEGRADATION OF HALOGENATED HYDROCARBONS BY SOLUBLE METHANE MONOOXYGENASE

STATEMENT REGARDING FEDERALLY SPONSORED RESEARCH

The invention described herein was made with the assistance of the National Institute of General Medical Sciences, National Institutes of Health Grant Nos. GM40466 and GM24689, and by a grant from the Center for Biological Process Technology of the University of Minnesota sponsored by the National Science Foundation. The Government has certain rights in the invention.

This is a Continuation of Ser. No. 07/886,608 filed May 20, 1992, now abandoned which is a divisional application of Ser. No. 07/814,202, filed Dec. 20, 1991, now U.S. Pat. No. 5,196,339, which is a Continuation of Ser. No. 07/384,859, filed Jul. 21, 1989, now abandoned, which in turn is a Continuation of Ser. No. 07/272,538, filed Nov. 17, 1988, now abandoned.

FIELD OF THE INVENTION

This invention relates to methods of biologically degrading halogenated hydrocarbon compounds including trichloroethylene (TCE), wherein said methods utilize a soluble methane monooxygenase or the methane-oxidizing bacterium which comprises the soluble methane monooxygenase.

BACKGROUND OF THE INVENTION

Halogenated hydrocarbon compounds are high-volume products of the chemical process industry; for example, more than 6 million metric tons of trichloroethylene (TCE), tetrachloroethylene (PCE), trichloroethane, carbon tetrachloride (CT), and chloroform (CF) are produced (in the United States) each year. Those halogenated hydrocarbon compounds most frequently found in groundwater are low molecular weight aliphatic halogenated hydrocarbons: TCE, dichloroethane (DCA), trichloroethane, and PCE. Many of these aliphatic halogenated hydrocarbon compounds, including TCE, have been listed as priority pollutants by the U.S. Environmental Protection Agency, and are known or suspected carcinogens and mutagens. Haloforms (halogenated derivatives of methane) are also frequently detected in groundwaters and drinking waters. Some haloforms are produced during chlorination of water supplies, but inadequate disposal techniques or accidental spillage may also be responsible for the presence of these haloforms.

Several of the halogenated hydrocarbon compounds mentioned above are resistant to biodegradation in aerobic subsurface environments, or their biological transformations are incomplete under anaerobic conditions. For example, under anaerobic conditions, TCE and PCE are known to undergo partial bioconversion to vinyl chloride, a compound which is as much or more of a problem as the original contaminants. Wilson and Wilson, *Appl. Env. Microbiol.*, 49:242–243 (1985).

Current technology for reclaiming groundwater polluted with these halogenated hydrocarbon compounds involves pumping water to the surface and stripping out the contaminants in aeration towers, or removing the pollutants on a sorbent. The former process is not permitted in some states, and the latter is expensive and involves the production of concentrated toxic materials that may present future problems.

In an alternative reclamation method, acetate-degrading methanogenic bacteria have been reported to degrade halogenated hydrocarbon compounds. Chloroform (CF), bromodichloromethane (BDCM), dibromochloromethane (BDCM), bromoform (BF), carbon tetrachloride (CT), 1,1,1-trichloroethane (1,1,1-TCA), 1,1,2,2-tetrachloroethane (1,1,2,2-TECE), and PCE have all been substantially degraded under methanogenic conditions utilizing an anaerobic column with acetate employed as the primary substrate in a medium seeded with a methanogenic mixed bacterial culture. A continuous-flow, fixed-film laboratory scale column operated under these conditions with a 2-day retention time substantially removed these compounds present at column influent concentrations ranging from about 15–40 $\mu$g/l. The acclimation period required for significant removal of CF, 1,1,1-TCA, and 1,1,2,2-TECE was about 10 weeks. Bouwer and McCarty, *Appl. Env. Microbiol.*, 45:1286–1294 (1983).

Other anaerobic bacteria are also known to degrade halogenated hydrocarbon-containing compounds. For example, the anaerobic bacteria *Methanobacterium thermoautotrophicum* and *D. autotrophicum* have been shown to convert carbon tetrachloride to di- and trichloromethane, and to partially dehalogenate other chlorinated aliphatic compounds. Egli et al., *FEMS Microbiol. Letter*, 43:257–261 (1987). The above results indicate that the use of methanogenic or other anaerobic bacteria to completely degrade all halogenated hydrocarbons is not commercially viable. These organisms exhibit slow rates of halogenated hydrocarbon destruction, even at low initial concentrations of the hydrocarbons, and are difficult to work with given that anaerobic conditions are required.

Additionally, chloroform is oxidized at rates of 35 nano-moles per gram of cells per minute by the aerobe *Methylococcus capsulatus* Bath. Higgins et al., *Nature*, 286:561–564 (1980); Haber et al., *Science*, 221:1147–1153 (1983). Similar rates of degradation were observed for other haloforms except for carbon tetrachloride, which was not oxidized by *Methylococcus capsulatus* Bath. Higgins et al., supra; Haber et al., supra.

Certain methane-oxidizing bacteria are known to degrade chlorinated haloforms and halogenated hydrocarbon compounds. For example, soil columns exposed to a surface mixture of 0.6% natural gas (primarily methane) in air for 3 weeks, and having water containing TCE at an average concentration of 150 $\mu$g/l added to the column influent at the end of the 3-week acclimation period, resulted in less than 5% of the applied TCE passing through the soil. Wilson and Wilson, supra. A methane-utilizing mixed culture isolated from a marsh has also recently been shown to completely oxidize TCE, vinyl chloride, vinylidene chloride, and dichloroethylene to carbon dioxide. Fogel et al., *Appl. Env. Microbiol.*, 51:720–724 (1986). However, the rate of TCE degradation reported by Fogel et al. was very slow, approximately 2.5 $\mu$moles per hour per gram of cells. Additionally, tetrachloroethylene was not oxidized by the mixed culture.

The above studies indicate that several chlorinated haloforms and halogenated hydrocarbon compounds are degradable by combined aerobic/anaerobic incubation under the proper conditions. However, the real potential of methane-oxidizing bacteria, or methanotrophs, for rapidly biodegrading halogenated hydrocarbon compounds such as TCE has not yet been exploited. For example, when TCE was added to the soil column used by Wilson and Wilson, supra, the soil had previously been acclimated to the natural gas mixture for 3 weeks. Similarly, the acclimation period required for significant removal of 1,1,1-TCA and 1,1,2,2 TECE in the Bouwer and McCarty study was about 10 weeks.

It has been known for some time that obligate methanotrophs derive no energy from metabolism of compounds other than methane. Haber et al., supra; Higgins et al., supra. However, methanotrophs are able to degrade numerous hydrocarbon compounds. The ability of methanotrophs to oxidize a wide range of compounds has been associated with the lack of specificity of methane monooxygenase (MMO), an enzyme produced by methanotrophs. Haber et al., Supra; Higgins et al., Supra. The MMO system of methanotrophic bacteria catalyzes the cleavage of $O_2$ and incorporation of one oxygen atom into methane to produce methanol.

The MMO system of methanotrophic bacteria can exist in either a soluble or a particulate (i.e., membrane-bound) form, depending on growth conditions. Burrows et al., *J. Gen. Microbiol.*, 130:3327-3333 (1984), reported that copper availability during the growth of the methanotrophic bacterium *Methylosinus trichosporium* OB3b (Mt OB3b) determined the intracellular location of its MMO (i.e., whether MMO activity was located in the particulate or the soluble fraction of the bacterium). However, the tendency of methanotrophic bacteria cells to elaborate only the membrane-bound (particulate) form of MMO has been a recurring problem in the purification of soluble MMO in quantity. Fox and Lipscomb, *Biochem. and Biophys. Res. Comm.*, 154:165-170 (1988). Burrows et al., supra, reported that the particulate form of the MMO of Mt OB3b differed from the soluble form of the enzyme in that the particulate MMO was unable to oxidize aromatic or alicyclic hydrocarbon compounds. Both the particulate and soluble forms of the MMO of Mt OB3b were shown to oxidize methane, propene, and various n-alkanes.

To date, however, no one has fully exploited the degradation ability of methanotrophic bacteria, nor in particular the degradation ability of the soluble form of the MMO produced by these bacteria, in order to both rapidly and completely degrade halogenated hydrocarbon compounds. For example, the rates of TCE degradation by methanotrophic bacteria reported thus far are unsatisfactorily slow and thus impractical for commercial use. Rates of TCE degradation reported under optimal conditions barely exceed 100 μmoles per hour per gram of cells. Fogel et al., supra; Nelson et al., *App. Env. Microbiol.*, 54:604-606 (1988); Nelson et al., *App. Env. Microbiol.*, 52:383-384 (1986). The time course of methanotrophic attack upon TCE reported in past studies suggests that TCE is in some way toxic to the bacteria cells, or to the enzymes functional in TCE degradation.

Accordingly, there is a need for a method to rapidly and completely degrade halogenated hydrocarbon compounds such as TCE by employing the soluble form of MMO, or by employing a methanotrophic bacterium which has been cultured in such a way as to produce the soluble MMO.

SUMMARY OF THE INVENTION

The present invention provides a method of microbial degradation of a halogenated hydrocarbon compound. The method comprises contacting the halogenated hydrocarbon compound with an amount of a methane-oxidizing bacterium effective to completely degrade halogenated hydrocarbon compounds such as TCE at a rate from about 500 to about 10,000 micromoles per hour per gram of cells. The methane-oxidizing bacterium is cultured under continuous culture conditions in which the bacterium is exposed to a continuous-flow gas mixture of air and methane in a ratio of about 25:1-1:10, respectively. The continuously cultured bacterium produces a soluble methane monooxygenase (MMO).

Preferably, rates of halogenated hydrocarbon degradation according to the present invention are from about 1,000 to about 9,000 micromoles per hour per gram of cells. In a preferred embodiment we have achieved rates of TCE degradation of 2000 to 4000 micromoles per hour per gram dry weight of *Methylosinus trichosporium* OB3b cells. The present invention provides for degradation of halogenated hydrocarbons present in initial concentrations of up to 10,000 micromoles/l and preferably provides for degradation of halogenated hydrocarbon compounds such as TCE at initial concentrations from trace amounts of TCE up to about 1,000 micromoles/l. Moreover, the continuously cultured cells produce soluble MMO at cell densities well below the cell densities required in other studies.

Further, in a preferred embodiment, *Methylosinus trichosporium* cells are employed in amounts of from about 0.10g/l to about 20g/l, most preferably in amounts of from about 0.2 to 2.0 g/l. The air/methane mixture used for continuous culturing can vary. We have found that preferably, degradation of TCE is stimulated when methane is present in amounts from about 1 to about 20% of saturation.

The present method is advantageous in that it both rapidly and completely degrades halogenated hydrocarbon compounds such as TCE. The continuous culture conditions employed by the present method to culture the methane-oxidizing bacterium ensure that TCE will be completely degraded by the bacterium when the concentration of TCE is significant. Additionally, the utilization of these continuous culture conditions provides for the generation of a methane-oxidizing bacterium which produces sufficient quantities of the soluble form of MMO. Using the continuous culture conditions of the present invention the amount of MMO in the cultured cells is from about 5 to 30% of the weight of dry cells.

The present invention also provides a method of cultivating a methane-oxidizing bacterium capable of completely degrading a halogenated hydrocarbon compound. The method comprises continuously culturing a methane-oxidizing bacterium so that the bacterium produces soluble MMO in an amount effective to completely degrade the halogenated hydrocarbon compound. Continuous culture conditions include exposure to a gas mixture of air and methane in a ratio from about 25:1 to about 1:20 preferably from about 10:1 to about 1:2, and most preferably about 2.1:1. Preferably, the amount of MMO in the culture cells is from about 5% to about 30% of the weight of dry cells Further provided by the present invention is a method of degrading a halogenated hydrocarbon compound using methane monooxygenase, the method comprising continuously culturing a methane-oxidizing bacterium; separating a soluble methane monooxygenase therefrom; purifying the soluble methane monooxygenase to yield the purified components reductase, component B, and hydroxylase; adding the purified components to an aqueous slurry of the halogenated hydrocarbon compound to form a mixture; and reacting the mixture for a period of time sufficient to completely degrade the halogenated hydrocarbon compound.

Other features and advantages of the invention will be apparent from the following detailed description and appended claims.

DETAILED DESCRIPTION OF THE INVENTION

Halogenated Hydrocarbon-Containing Compounds

Figure 1:
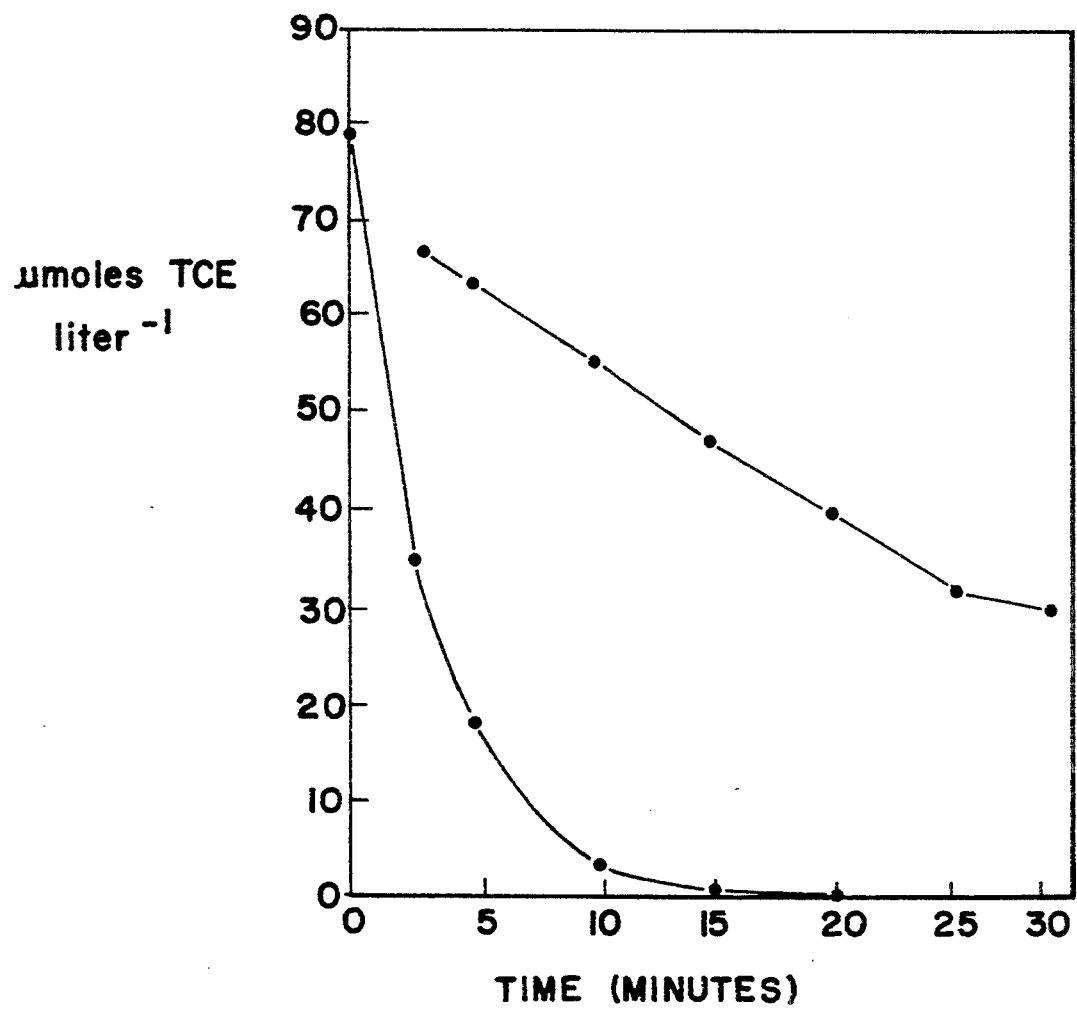
FIG. 1 is a graphical representation of the time course of TCE degradation by continuously cultured Mt OB3b, determined at two different values of bacterial cell density.

The present invention provides a method of rapidly and completely degrading a halogenated hydrocarbon compound. Although the present invention preferably provides a method of degrading trichloroethylene (TCE), other halogenated hydrocarbons which may be degraded by the present method include, but are not limited to, tetrachloroethane, tetrachloroethylene (PCE), trichloroethane, dichloroethane (DCA), and chloroform.

The preferred halogenated hydrocarbon compound of the present invention, TCE (1,1,2-trichloroethene), is an aliphatic halogenated hydrocarbon with the chemical structure $HClC=CCl_2$. TCE is primarily used in industry as a fire-resisting solvent. It can be produced by removal of one molecule of hydrogen chloride from acetylene tetrachloride with alkali.

Methanotrophic Bacteria

The present invention utilizes methane-oxidizing bacteria to degrade the halogenated hydrocarbon-containing compounds described above. Preferably, bacteria of the strain *Methylosinus trichosporium* OB3b (Mt OB3b) are utilized which produce the soluble form of the enzyme methane monooxygenase (MMO) *Methylssinus trichosporium* strain OB3b was placed on deposit with American Type culture Collection (ATCC), Rockville, Md. on Feb. 15, 1995, under ATCC accession number 55658. Other methane-oxidizing bacteria which produce MMO may be useful in the present invention. These other bacteria include, but are not limited to, *Methylosinus sporium, Methylocytis parvus* and other species of the genera Methylomonas, Methylbacter and Methylococcus.

Mt OB3b is an obligate type II methanotrophic bacterium which is capable of growing on methane as its sole source of carbon and energy. This bacterium was discovered by Whittenbury et al., *J. Gen. Microbiol.*, 61:205-218 (1970). It is a gram-negative rod- or pear-shaped bacterium that forms exospores and which is typically found in rosette-shaped clusters of several cells. Mt OB3b colonies on methane media are white-yellow in color. Like other type II methanotrophs, Mt OB3b contains a complete tricarboxylic acid cycle, and utilizes the serine pathway for formaldehyde assimilation. The DNA of Mt OB3b has a G+C content of 62.5 mol-%. Mt OB3b grows at 37° C., but not at 45° C. Growth of Mt OB3b is not stimulated by yeast extract or by other multi-carbon compounds tested by Whittenbury et al., supra. Mt 0B3b is motile with polar tuffs of flagella. Capsules formed by Mt OB3b consist of short fibers radiating from the cell wall and do not respond to polysaccharide stain. The Mt OB3b strain used in the present invention was obtained from Professor R. Whittenbury, Warwick University, United Kingdom and has been deposited with the National Collection of Industrial Bacteria, Aberdeen, Scotland and assigned number NC1B-11131.

Degradation of Halogenated Hydrocarbon Compounds

The present invention provides a method of microbial degradation of a halogenated hydrocarbon compound. The method comprises contacting the halogenated hydrocarbon compound, preferably TCE, with an amount of a methane-oxidizing bacterium, preferably Mt OB3b, effective to completely degrade the halogenated hydrocarbon compound at a rate from about 500 to about 10,000 μmicromoles per hour per gram of cells. In the method of the present invention the methane oxidizing bacterium is cultured under continuous culture conditions so as to produce soluble MMO. As used herein an effective amount of methane oxidizing bacterium is an amount of the bacterium capable of completely degrading TCE at the rates stated herein. Further, as used herein, the phrase "continuous culture conditions" means that the methane-oxidizing bacterium has been cultured in a continuously replaced medium that is exposed to a continuous flow of a gas mixture comprising air and methane in a ratio of about 25:1–1:20, respectively; preferably about 10:1–1:2; and most preferably about 2.1:1. Continuous culture and growth parameters are as described in Cornish, *J. Gen. Micro.*, 130:2565–2575 (1984) with a dilution rate of continuous culture of about 0.1 volumes/volume culture per hour. The air-to-methane ratio of the gas mixture may be varied, and we have found that methane at concentrations between 1–20% of saturation greatly stimulate TCE oxidation.

We have determined that conventional (i.e. shake flask, non-continuous) methods of culturing the methane-oxidizing bacterium utilized in the present invention prove less than satisfactory in terms of the extent of removal of TCE from media comprising any significant initial concentration of TCE. More specifically, we have found that at initial TCE concentrations of one ppm or higher, oxidation of TCE ceased at about 50% removal when Mt OB3b grown by conventional methods (shake flask) was utilized.

The halogenated hydrocarbon compound to be degraded by the present method is preferably contacted with the methane-oxidizing bacterium in an aqueous media which comprises about 0.10–20 g/l of the methane-oxidizing bacterium, more preferably from about 0.2 to 2.0g/l of the methane-oxidizing bacterium is used. The preferred aqueous media used in the present invention is referred to herein as Higgins media. The method of preparing Higgins media is disclosed by Cornish et al., *J. Gen. Micro.*, supra. The recipe utilized in the present invention for the preparation of Higgins media is given in Example 1 below. Higgins media is classified as a minimal salts nitrate media, and contains about 250 $\mu$g/l of $Cu^{2+}$. Other aqueous media suitable for use in the present invention may include, but are not limited to those described by Pat et al., *Int. J. Systematic Bacteriol.*, 26:226-229 (1976) as well as AMS and NMS minimal media; see Whittenburg et al., *J. Gen. Microlial.*, supra.

The present method provides for complete degradation of a halogenated hydrocarbon compound, preferably TCE, present at initial concentrations up to 10,000 micromoles/l and more preferably at concentrations of from trace amounts to 1000 micromoles/l. These concentration values represent the initial concentration of the halogenated hydrocarbon compound in a solution comprising the hydrocarbon compound, the bacterium, and the aqueous media. It is to be understood that trace amounts refers to lower limits of detection by assay techniques described in the Examples herein.

The present method achieves rates of TCE degradation of at least 500 $\mu$moles per hour per gram of cells with a range of TCE degradation rate from about 500-10,000 $\mu$moles per hour per gram of cells; preferably the range is from about 1000-9000 moles per hour per gram of cells. More preferably the present method achieves rates of TCE degradation about 2000-4000 moles per hour per gram of cells, where "gram of cells" means gram of methane-oxidizing bacterium cells on a dry weight basis.

Cultivation of Methane-Oxidizing Bacteria

The present invention is further directed to a method of cultivating a methane-oxidizing bacterium which is capable of completely degrading a halogenated hydrocarbon compound, preferably TCE. The method comprises culturing the methane-oxidizing bacterium, preferably Mt OB3b, under continuous culture conditions in a suitable minimal salts media, such as Higgins media. The continuous culture conditions comprise exposing the bacterium to a continuous-flow gas mixture of air and methane in a ratio of about 25:1-1:20, preferably about 10:1-1:2, and most preferably about 2.1:1. Preferably, the gas mixture during degradation of TCE comprises methane at a concentration of about 1-20% of saturation. The present method provides that the continuously cultured methane-oxidizing bacterium will comprise an amount of soluble MMO which is effective to completely degrade the halogenated hydrocarbon compound. Preferably, the amount of soluble MMO produced in the continuously cultured bacterial cells is from about 5-30% of the weight of the dry bacterial cells.

Methane Monooxygenase

The methanotrophic bacterium Mt OB3b can comprise both a particulate (i.e., membrane-bound) and a soluble form of the enzyme methane monooxygenase (MMO). Tonge et al., *FEBS Letters*, 58:293-299 (1975), reported that MMO is located in the particulate fraction of Mt OB3b, and that MMO could be solubilized from the particulate fraction by treatment with phospholipase D, sonication, or Triton X-100. Tonge et al. also reported that ascorbate was an effective electron donor substitute for NADH both in crude extracts of Mt OB3b or in its particulate fraction, but that associated CO-binding cytochrome c seemed to be essential for MMO activity. However, Stirling and Dalton, *Eur. J. Biochem.*, 96:205-212 (1979), later reported that the MMO in cell-free extracts of Mt OB3b appeared to be soluble, and that it required NAD(P)H as an electron donor for activity. Further, they reported that ascorbate was not an effective electron donor for the MMO of Mt OB3b. Stirling et al., *Biochem J.*, 77:361-364 (1979), also characterized MMO in several ways including its substrate specificity when present in crude abstracts of Mt OB3b.

MMO catalyzes the first step in the oxidation metabolism of methane, in which $O_2$ is cleaved and one oxygen atom is inserted into a C-H bond of methane to yield methanol. Fox et al., *J. Biol. Chem.*, 263:10553-10556 (1988). The reaction stoichiometry of this step is shown below:

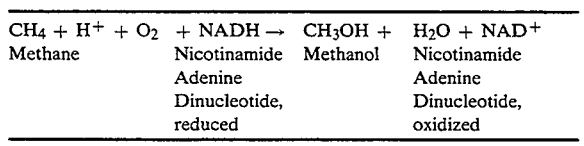

| $CH_4$ + $H^+$ + $O_2$ | + NADH $\rightarrow$ | $CH_3OH$ + | $H_2O$ + $NAD^+$ |
|---|---|---|---|
| Methane | Nicotinamide Adenine Dinucleotide, reduced | Methanol | Nicotinamide Adenine Dinucleotide, oxidized |

Fox and Lipscomb, *Biochem. & Biophys. Res. Comm.*, 154:165-170 (1988), incorporated by reference herein provided a purified MMO from Mt OB3b and resolved the MMO system of Mt OB3b into three components, all three of which they found were required for reconstituting methane-oxidizing activity in vitro. These components were denoted by Fox and Lipscomb as the reductase, component B, and the hydroxylase, respectively. The cells of Mt OB3b utilized in the purification process of Fox and Lipscomb were grown in continuous culture as described by Cornish et al., *J. Gen. Micro.*, 130:2565-2575 (1984). The Mt OB3b thus cultured reproducibly expressed the soluble form of MMO, and could be cultured in high yield.

Degradation of Halogenated Hydrocarbons by Purified Methane Monooxygenase

We have found that purified MMO components oxidize TCE. Accordingly, the present invention envisions a method of degrading a halogenated hydrocarbon compound by continuously culturing a methane-oxidizing bacterium, preferably Mt OB3b, by exposing the bacterium to continuous culture conditions including a continuous-flow gas mixture comprising air and methane in a ratio of about 25:1-1:20, preferably about 10:1-1:2, and most preferably about 2.1:1, and wherein the bacterial thus cultured comprises soluble MMO in an amount from about 5-30% of the weight of the dry bacterium cells; separating the soluble MMO from the continuously cultured bacterium cells, purifying the soluble MMO to yield purified components comprising reductase, component B, and hydroxylase; adding an effective amount of the purified components, preferably in a ratio of about 110:13:250 by weight of the three Components, respectively, to an aqueous slurry of the halogenated aliphatic hydrocarbon compound, preferably TCE, to form a mixture; and reacting the mixture for a period of time sufficient to completely degrade the halogenated aliphatic hydrocarbon compound.

The invention will be further described by reference to the following detailed examples.

Example I

Preparation of Higgins Media[1]

[1] The method of preparation of Higgins media is disclosed by Cornish et al., *J. Gen. Micro.*, 130:2565-2575 (1984).

In order to provide a medium for the cultivation of the methane-oxidizing bacterium suitable for use in the present invention, the following solutions were prepared and stored at 4° C.:

| Ingredient: | Volume %: |
|---|---|
| 100x Higgins Salts Solution | |
| $NaNO_3$ | 85 |
| $K_2SO_4$ | 17 |
| $MgSO_4.7H_2O$ | 3.7 |
| $CaCl_2.2H_2O$ | 0.7 |
| 100x Higgins Phosphate Solution | |
| $KH_2PO_4$ | 53.0 |
| $Na_2HPO_4$ | 86.0 |
| Adjust this solution to pH 7.0. | |
| 500x Higgins Trace Metals Solution | |
| $ZnSO_4.7H_2O$ | 0.287 |
| $MnSO_4.7H_2O$ | 0.223 |
| $H_3BO_3$ | 0.062 |
| $NaMoO_4.2H_2O$ | 0.048 |
| $CoCl_2.6H_2O$ | 0.048 |
| KI | 0.083 |
| $CuSO_4.5H_2O$ | 0.125 |
| Add 1 ml of 1 mM $H_2SO_4$ per liter of Trace Metals Solution. | |
| 1000x Higgins Iron Solution | |
| Ingredient: | Concentration: |
| $FeSO_4.7H_2O$ | 1.12 g/100 ml |
| Add 5 ml of 1 mM $H_2SO_4$ per 100 ml of Higgins Iron Solution. | |

Ten ml of Higgins Salts Solution, 10 ml of Higgins Phosphate Solution, and 2 ml of Higgins Trace Metals Solution were mixed together per liter of media desired. Distilled water was added to make up the final volume. If agar plates were being made, 17 g of purified agar per liter of liquid media was added. The mixture was autoclaved for 20 minutes with slow exhaust. When the media had cooled sufficiently to pour plates, or prior to inoculation, 1 ml of Higgins Iron Solution was added by filter sterilization per liter and mixed carefully. Higgins media agar plates were marked with a red stripe.

Example II

Continuous Culture of Mt OB3b

A continuous culture of Mt OB3b was performed in which the bacterium grew at rate of approximately 10 hours per generation on Higgins medium prepared as in Example I. The continuous culture was grown in a chemestat growth chamber having a 0.185 liter volume. J. Depamphillis and R. Hanson, *J. Bacterial.*, 98:222-225 (1969), incorporated by reference herein.

Figure 3:
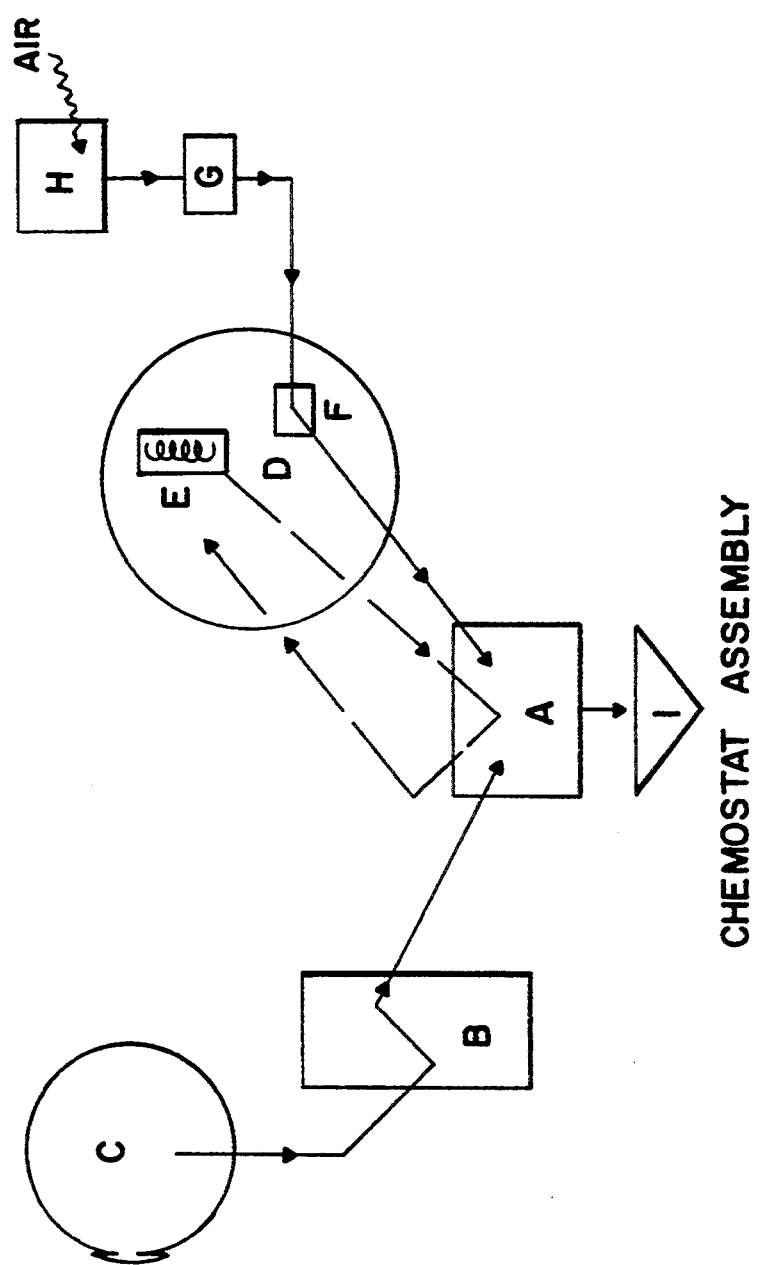
FIG. 3 shows a chemostat assembly of the type used to grow cultures in accordance with the present invention.

The apparatus consisted of a water jacketed growth chamber supplied with sterile, warm moist air and a constant supply of medium (See FIG. 3 in which arrows indicate the flow of medium air, warmed water and effluent: oxygen was supplied from the atmosphere). Referring to FIG. 3, the alphabetic references describe: (A) chemostat growth flask (B) medium pump; (C) medium reservoir; (D) constant temperature bath; (E) constant temperature heater pump; (F) air humidifying chamber; (G) air sterilizing chamber, (H) air pump and (I) culture collection flask.

a. Growth Chamber

Figure 4:
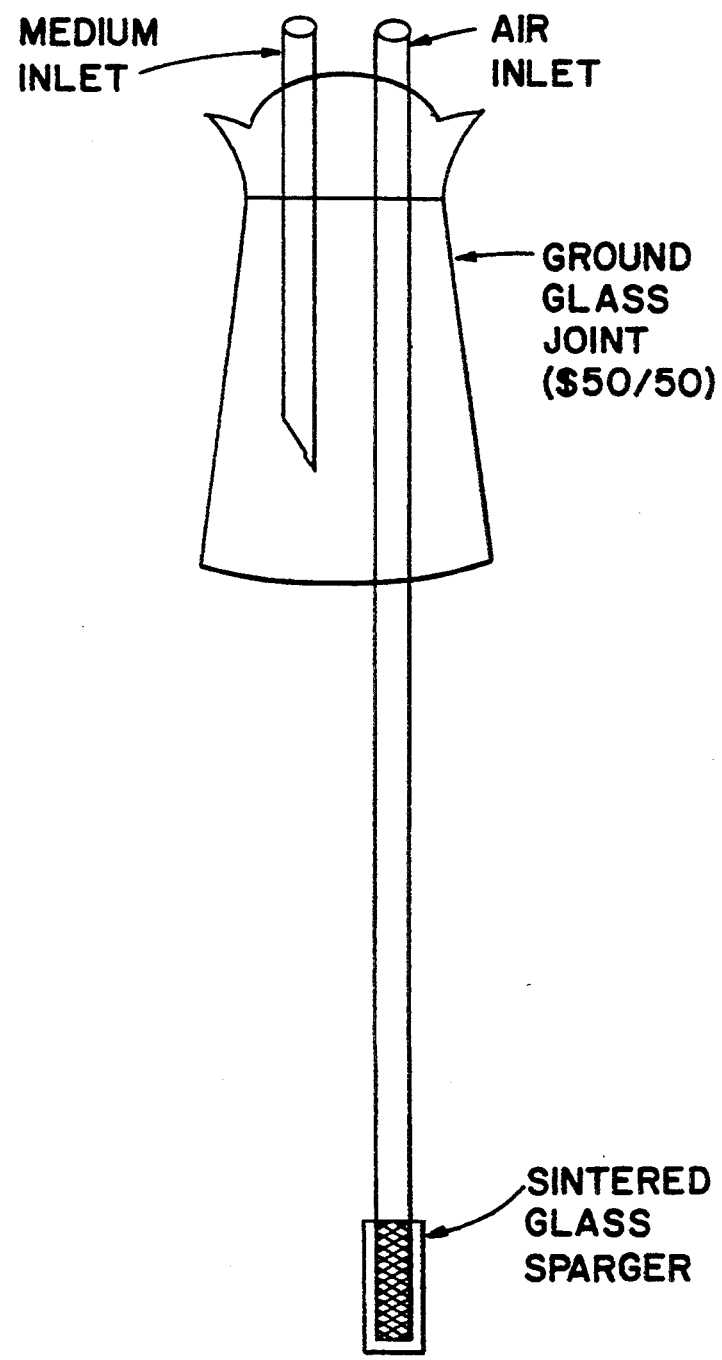
FIG. 4 shows the head of a chemostat growth flask of the type used to grow cultures in accordance with the present invention.
Figure 5:
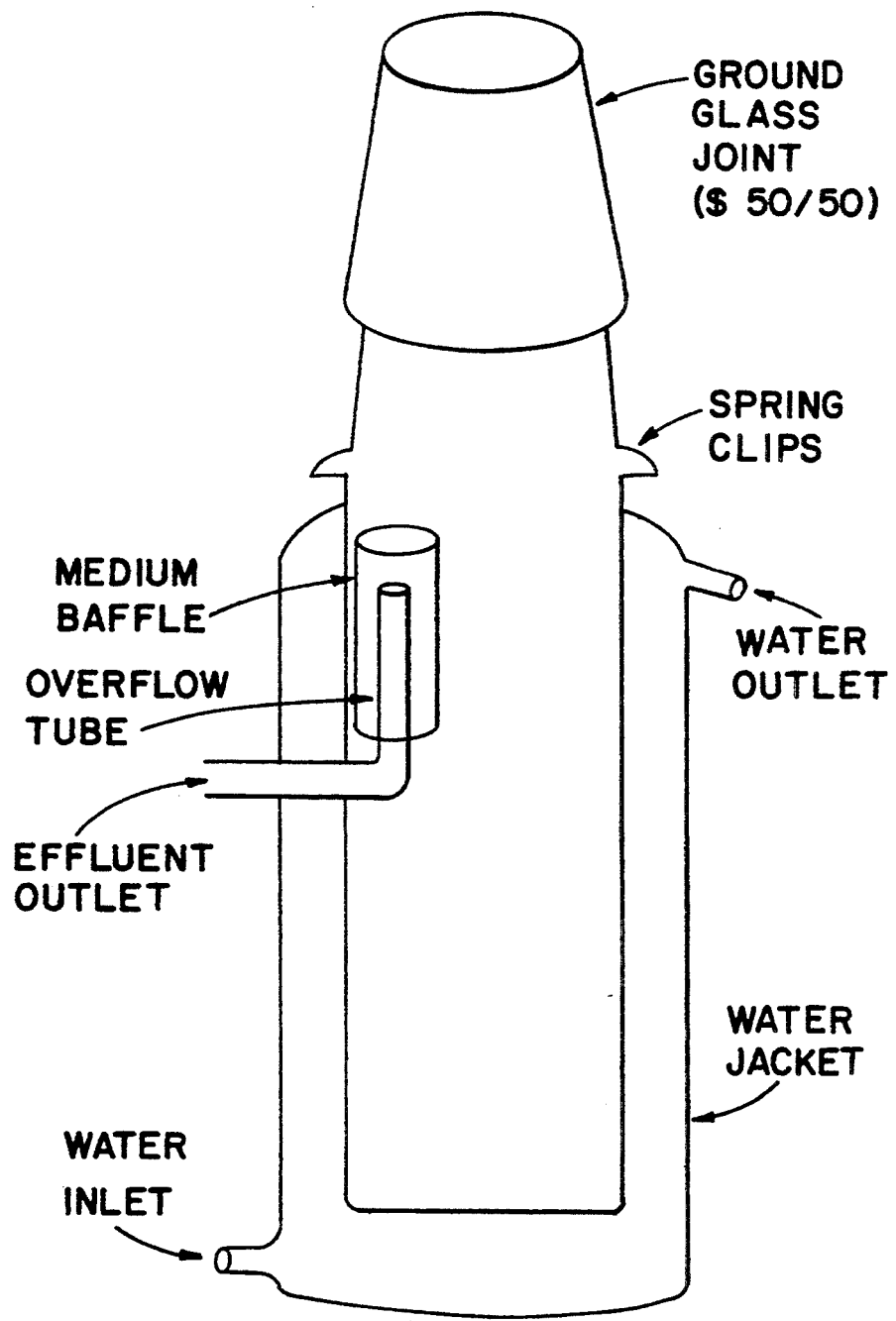
FIG. 5 shows the body of a chemostat growth flask of the type used to grow cultures in accordance with the present invention.

This chamber is composed of two parts; a head section (FIG. 4) and a body section (FIG. 5). The head contains two parts, one for medium and one for air, and is fitted tightly onto the body section by a ground glass joint. The body is water jacketed and has an overflow device to maintain a constant volume in the chamber. The entrance to this overflow duct is shielded by a glass baffle which helps keep the volume in the chamber constant by preventing the slight amount of foam produced by sparging from leaving the overflow. The maximum volume of the growth chamber was 200 ml.

b. Constant Temperature Apparatus

A. B. Braun Thermomix II (Melsungen, Germany) constant temperature water pump was used to circulate warmed water (30° C.) through the water jacket of the growth chamber. This warmed water also heats the air which is passed into the growth flask (See FIG. 3). The Thermomix II is sensitive to changes of 0.1° C so the temperature variation is well within the limits of temperature control required.

c. Aeration System

Bubbles of air were used to supply oxygen and aid in the mixing of the bacterial culture. Air was pumped from the atmosphere by a B 2-F Model Aquarium Pump (Eugene G. Danner Mfg. Co.). The air passed first into a wash bottle containing 1% $HgCl_2$ via a sintered glass sparger and then through a warming bath (30° C.) of sterile water contained in a wash bottle which was partially submerged in a water bath. The air then passed into the growth chamber via a sintered glass gas dispersion tube.

25 ml of Mt OB3b cells were inoculated into 0.185 l of Higgins media and incubated in the growth chamber at 30° C. New media was continuously added and expelled. The continuous air feed was supplied with an aquarium pump and methane from a pressurized tank. The gas mixture was applied in a volume ratio of approximately 1:1 ($CH_4$:air). The growth vessel was stirred vigorously. Mt OB3b cells were grown to various turbidities and measured on a Spectronic 20 spectrometer (600 nm) at which time two-phase (Headspace) assays were performed.

Example III

Assaying for Rate of TCE Degradation

1. Incubation Without Headspace[2]

[2] A convenient liquid-liquid extraction method for the determination of halomethanes in water at the parts-perbillion level is disclosed by Henderson, J. E., G. R. Peyton and W. H. Glaze, in L. H. Keith, ed., Identification and Analysis of Organic Pollutants in Water, Ann Arbor Science Publishers, pp. 105-111 (1976).

General Protocol:

Each culture of Mt OB3b was added to 1.8 ml serum bottle prewarmed to 30° C. and sealed with an 11 mm teflon-lined rubber septa. For comparisons requiring similar initial dissolved oxygen levels, anaerobic make-up media (usually 0.6 ml) was added to the bottles first and then the bottles were sealed. Air-saturated 30° C. Higgins media prepared as in Example I was added via gas-tight syringe (1.0 ml), while 1 atm pressure was maintained by allowing air to bleed through a 25 gauge needle. Finally, culture was added (concentrated to give desired density) while remaining headspace was bled out through the 25 gauge needle. TCE was added with a syringe at the bottom of the sealed bottle, with a syringe at top of the bottle removing equivalent volume of culture. The assay time course was started with TCE (substrate) addition. Incubation was performed at 30° C. with agitation at 200 rpm on a platform shaker.

Assays were terminated by extraction at desired time points. The liquid-liquid extraction technique used 0.6 ml of pentane containing 1,2-dibromoethane as an internal standard added via gas-tight syringe to inverted assay bottle, while a second syringe with a needle below first needle level collected displaced solution. Partitioning was brought to equilibrium by centrifugation of bottles at 5000 rpm for 10 min. The organic layer was removed by gas-tight syringe and placed in a 1 ml serum bottle for chromatographic analysis. In some cases, dilution of sample or split injection was necessary. Electron-capture detection was preferred. The following gas chromatography operating parameters were used:

TABLE I

| Gas Chromatography Parameters | |
|---|---|
| GC: | HP5790A (with ECD) |
| Column: | Non-Pakd RSL-160 Thick Film Capillary (Alltech) |
| Injection Temperature: | 150° C. |
| Detection Temperature: | 250° C. |
| Ramping: | 35° C. (1st min), ramped to 120° C. at 15° C./min |
| Carrier Gas: | $H_2$ |
| Carrier Gas Flow: | 8 ml/min |
| Injection Volume: | 1 ml |

No-Headspace Assays of TCE Degradation:

The following Tests 1, 2 and 3 were conducted according to the no-headspace assay procedure described generally above. A summary of the results of these 3 tests is given in Table II, below:

TABLE II

Summary of Results of No-Headspace Assays

| Test | Culture turbidity (Absorbence 600 nm) | Rate of TCE-utilization ($\mu$moles · hr$^{-1}$ · g cells$^{-1}$) (no headspace assay) |
|---|---|---|
| 1 | 1.310 | 336 |
| 2 | 1.410 | 1070 |
| 3 | 1.460 | 2400 |

The exact assay protocol used and the detailed results obtained in each test are given below.

Test 1—No-Headspace Assay

Protocol:

2 ml of Mt OB3b cell suspension grown in a chemostat (procedure) with absorbance $A_{600}=1.310$ were added to 8 ml of 30° C. Higgins media prepared as in Example 1 in prewarmed 120 ml serum bottles (1/5 dilution $A_{600}=0.252$). The bottles were evacuated and refilled with air having 0% methane. One bottle was heat-killed and used as a control.

1.79 ml of Mt OB3b cell suspension was added to sealed 1.8 ml serum bottles. 11.25 $\mu$l of 4 mM TCE stock was added to start the assay with a nominal initial TCE concentration of 25 $\mu$M. Bottles were sacrificed at 2.5, 5.0, 10.0 and 15.0 minutes by displacing 0.6 ml aqueous solution with pentane containing 1 ppm 1,2-dibromoethane as an internal standard.

The results of Test 1 are given in Table III, below:

TABLE III

| | Test 1 Results | |
|---|---|---|
| Time | [TCE], ppm | [TCE], $\mu$M |
| Run 1 Results: | | |
| Heat-killed control, 0% methane: | | |

TABLE III-continued

| | Test 1 Results | |
|---|---|---|
| Time | [TCE], ppm | [TCE], $\mu$M |
| 2.5 min | 1.836 | 13.97 |
| 5.0 min | 2.691 | 20.48 |
| 15.0 min | 2.883 | 21.94 |
| Run 2 Results: | | |
| 1/5 dilution, 0% methane: | | |
| 2.5 min | 2.103 | 16.01 |
| 5.0 min | 0.261 | 1.99 |
| 10.0 min | 0.255 | 1.94 |
| 15.0 min | 0.204 | 1.55 |

Test 2—No-Headspace Assay

Test 2 was performed following the same procedures described above for Test 1, except that 1/20 and 1/50 dilutions were performed. The results of Test 2 are given in Table IV, below:

TABLE IV

| Test 2 Results | | |
|---|---|---|
| $A_{600}$ = 1.410 from chemostat | | |
| 1/20 dilution $A_{600}$ = 0.069 | | |
| 1/50 dilution $A_{600}$ = 0.026 | | |
| Nominal initial TCE concentration = 25 $\mu$M | | |
| Time | [TCE], ppm | [TCE], $\mu$M |
| Run 1 Results: | | |
| Heat-killed control, 0% methane: | | |
| 2.5 min | 2.749 | 20.92 |
| 5.0 min | 2,861 | 21.77 |
| 10.0 min | 2.901 | 22.08 |
| 15.0 min | 3.132 | 23.84 |
| Run 2 Results: | | |
| 1/20 dilution, 0% methane: | | |
| 2.5 min | 4.227 | 32.17 |
| 5.0 min | 3.475 | 26.45 |
| 10.0 min | 2.843 | 21.64 |
| 15.0 min | 2.742 | 20.87 |
| Run 3 Results: | | |
| 1/50 dilution, 0% methane: | | |
| 2.5 min | 2.924 | 22.25 |
| 5.0 min | 1.843 | 14.03 |
| 10.0 min | 2.717 | 20.68 |
| 15.0 min | 3.183 | 24.22 |

Test 3—No-Headspace Assay

In prewarmed (30° C.) 120 ml serum bottles, 1 ml of Mt OB3b cell suspension grown in a chemostat ($A_{600}=1.460$) were mixed with 9 mls of 30° C. Higgins media prepared as in Example I. One bottle was prepared by adding "spent" media from the chemostat (decant media after pelleting cells with centrifugation—10,000 rpm for 10 minutes) rather than fresh Higgins media. The bottles were sealed with 20 mm teflon-lined rubber septa, evacuated and refilled with air (0% methane). One bottle was heat-killed and used as a control.

1.76 ml of Mt OB3b cell suspension was added to sealed 1.8 ml serum bottles (25 gauge needle used to equilibrate pressure). 45 $\mu$l of 4 mM TCE stock were added to start the assay. Bottles were incubated at 30° C. with agitation on a shaker bath. Bottles were sacrificed at 2.5, 5.0, 10.0, 15.0 and 20.0 mins by displacing 0.6 ml aqueous solution with pentane containing 1 ppm 1,2-dibromoethane as an internal standard. Analysis was performed on a HP 5790A GC using ECD.

The results of Test 3 are given in Table V, below:

TABLE V

Test 3 Results
$A_{600}$ = 1.460 from chemostat
1/10 dilution $A_{600}$ = 0.140
Nominal initial TCE concentration = 100 μM
(using 4 mM TCE stock in water)
Dry weight = 0.10 g · $l^{-1}$
Run 1 Results:
Heat-killed control, 0% methane:

| Time, min | [TCE], ppm | [TCE], μM |
|---|---|---|
| 2.5 | 15.679 | 119.33 |
| 5.0 | 14.713 | 111.98 |
| 10.0 | 14.760 | 112.34 |
| 15.0 | 15.230 | 115.91 |
| 20.0 | 14.691 | 111.81 |

| Time, min | [TCE], ppm | [TCE], μM | Rates μmoles · $h^{-1}$ · g cells$^{-1}$ |
|---|---|---|---|
| Run 2 Results: 1/10 dilution in Higgins media, 0% methane: | | | |
| 2.5 | 14.119 | 107.46 | |
| 5.0 | 14.651 | 111.41 | |
| 10.0 | 11.981 | 91.19 | |
| 15.0 | 8.406 | 63.98 | 3200 (10 min–15 min) |
| 20.0 | 7.208 | 54.86 | |
| Run 3 Results: 1/10 dilution in spent Higgins media from chemostat, 0% methane: | | | |
| 2.5 | 14.277 | 108.66 | |
| 5.0 | 13.757 | 104.70 | |
| 10.0 | 12.924 | 98.36 | |
| 15.0 | 8.543 | 65.02 | 3960 (10 min–15 min) |
| 20.0 | 7.650 | 58.22 | |

The rate at those times in the reactions when most rapid oxidation of TCE occurred was approximately 3500 μmoles/$h^{-1}$·g cells$^{-1}$. This rate was not stimulated by the addition of methane to the reaction mixture. The rate of TCE oxidation in the presence of methane over time is linear and TCE oxidation is more complete. TCE oxidation also occurs more rapidly in the presence of low concentrations of methane (Table VII). Therefore, it is believed that cells can oxidize TCE at rates of 10,000 μmoles·$h^{-1}$·g cells$^{-1}$ under optimal conditions.

2. Incubation with Headspace

Each culture of Mt OB3b was added in 2 ml quantities to 10 ml serum bottles. Bottles were sealed with 20 mm teflon-lined rubber septa. TCE was added to start the assay. Headspace accounted for 80% of total volume within bottles, but TCE concentration was added based on 2 ml aqueous phase. TCE resided principally in the headspace. All bottles were inverted in order to prevent possible TCE loss by trapping the compound in the headspace between the liquid phase and glass. Samples were incubated inverted at 30° C. with agitation (200 rpm on a platform shaker).

Preparation of GC Calibration Curves:

Headspace incubations were analyzed by direct injection of headspace into a gas chromatograph. This method may be performed without sacrificing a sample. It is important to prepare sound calibration curves for quantitation. The best method for external standardization is to prepare samples as if running an assay and heat-killing at 80° C. for 10 mins prior to TCE addition. Samples were incubated for 30 mins under test conditions to allow adequate time for TCE to partition among the numerous phases (air, water, cell material, and the like). Headspace samples were injected into a gas chromatograph using either FID or ECD. Numerous TCE concentrations were used to obtain a sound standardization curve.

Example IV

TCE Degradation with Headspace Assay

Headspace assays of TCE degradation were conducted by adding bacterial cells from the continuous culture described in Example II or cells diluted with spent Higgins medium (2 mls) into assay vials (10 ml vials).

Dilution of cells in spent Higgins medium had no effect on the rate of TCE oxidation. Therefore, there do not seem to be protective compounds in the medium.

Heat-killed controls indicated that no TCE was lost from the vials.

The rates of TCE utilization in two-phase head space assays are shown in Table VI, below. Rates were calculated from peak heights of recorder tracings from a gas chromatograph equipped with an electron capture detector. The gas chromatograph parameters reported in Table I herein were utilized.

TABLE VI

TCE Degradation in Two-Phase Assay

| Cell density in assay vials (g · $l^{-1}$) | Initial TCE conc. (micromolar) | Rate, micromoles TCE oxidized · g cells$^{-1}$ · hr$^{-1}$ |
|---|---|---|
| .695 | 22 | 281 |
| .521 | 22 | 308 |
| .347 | 22 | 465 |
| .173 | 23 | 461 |
| .070 | 22 | 808 |

Example V

Effect of Mt OB3b Cell Density on TCE Degradation Rate

In this example, the cell mass of the continuous culture (generated in Example II) increased to 0.825 g/l from 0.695 g/l. As shown in FIG. 1, the rate of TCE degradation at low cell densities increased to 1200 micromoles TCE removed·hr$^{-1}$·g cells$^{-1}$ at an initial TCE concentration of 80 μM.

The rate of methane oxidation by these cells during culturing was 2860 moles·hr$^{-1}$·g cells$^{-1}$.

The curves at two different Mt OB3b cell densities shown in FIG. 1 also illustrate that TCE oxidation was less complete at low cell densities than at high cell densities. This indicates that cells at high densities withstand toxic intermediates because there is more biomass available to react with the reactive intermediate compounds.

Alternatively, the slower rates of oxidation per unit mass at high cell densities may have limited the rate of production of toxic intermediates to a rate at which they were further degraded.

Example VI

TCE Degradation with Single Phase Assay

In order to test the hypothesis that gas transfer limited oxidation rates at high cell densities, the rate of TCE degradation was assayed in a single phase assay using techniques for no head space assay described in Example III. The assay was performed at a Mt OB3b cell density of approximately 0.160 g/l, and an initial TCE concentration of 80 μmoles. The rate of TCE oxidation was 2400 micromoles·hr$^{-1}$g cells$^{-1}$ or 315 mg·hr$^{-1}$·g cells$^{-1}$.

Example VII

Effect of Methane Present During TCE Degradation

Figure 2:
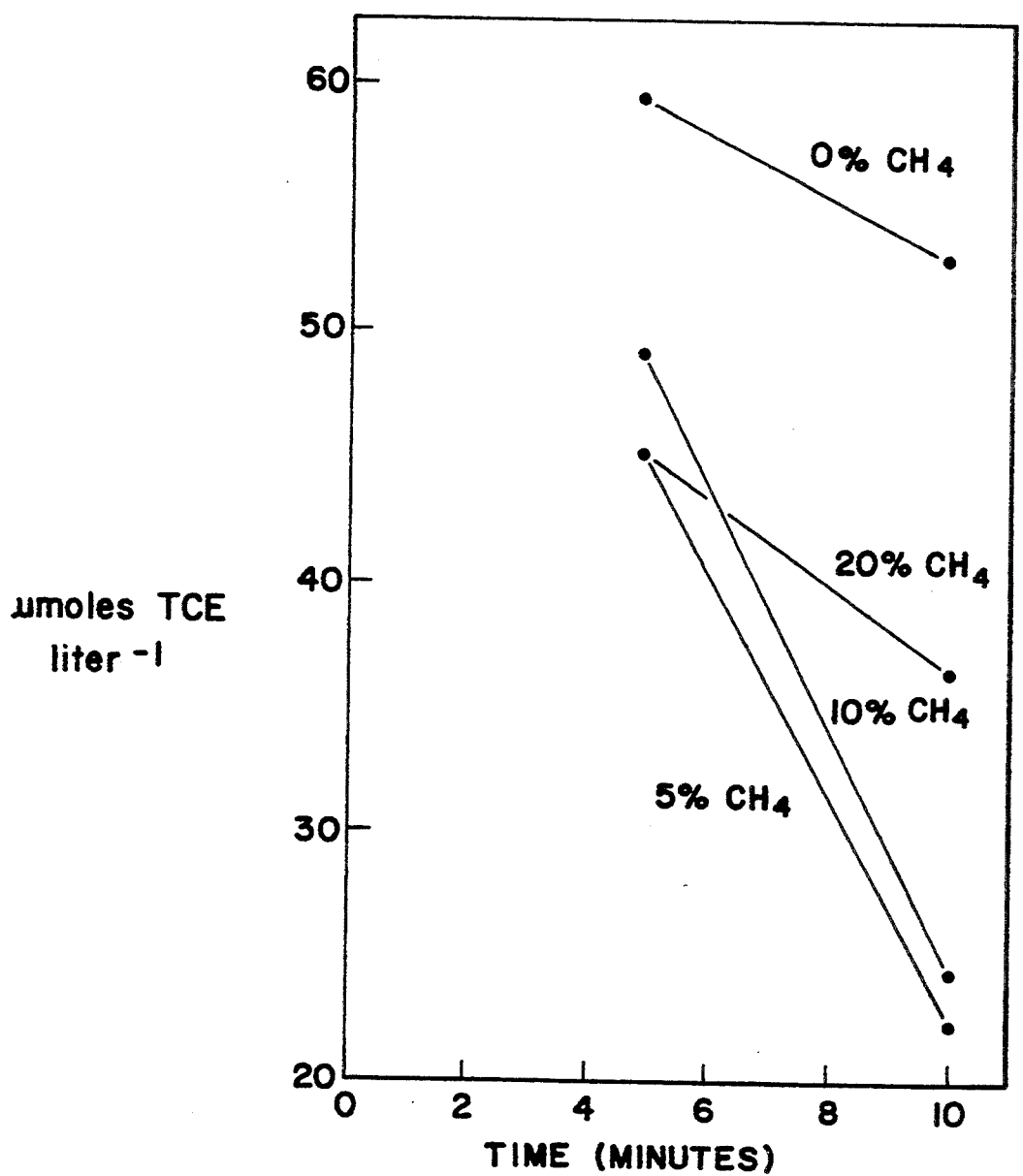
FIG. 2 is a graphical representation of the time course of TCE degradation by continuously cultured Mt OB3b in the presence of different levels of methane.

In this example the effect of methane present in the TCE oxidation vessel on the rate of oxidation of TCE was determined. A no head space assay of TCE degradation was performed according to the procedures of Example III in which the Mt OB3b cell density was approximately 0.16 g/l, and the nominal initial TCE concentration was 80 $\mu$M. The results are presented in Table VII, below and FIG. 2.

TABLE VII

| Rate of TCE Degradation in Presence of Methane | |
| --- | --- |
| Methane added to reaction system, (% saturation) | Rate of TCE oxidation, $\mu$moles $\cdot$ hr$^{-1}$ $\cdot$ g cells$^{-1}$ |
| none | 660 |
| 5% | 3350 |
| 10% | 3000 |
| 20% | 875 |
| 50% | 110 |

We have subsequently observed that some cell batches oxidize TCE at rate of approximately 4000 micro-moles.hr$^{-1}$.g cells$^{-1}$ without any methane present.

Example VIII

Effect of Initial TCE Concentration on TCE Degradation Rate

Mt OB3b cells were continuously cultured under the following conditions:

| | |
| --- | --- |
| Medium: | Higgins (prepared as in Example I) |
| Gas flow rates: | methane 45 ml/min |
| | air 135 ml/min |
| Culture volume: | 220 ml |
| Culture temperature: | 30° C. |

A TCE no head space degradation assay of the type in Example III was performed using these cells. The results are shown in Table VIII, below:

TABLE VIII

| Effect of Initial TCE Concentration on Rate of TCE Oxidation | |
| --- | --- |
| Concentration of TCE, $\mu$M | micromoles TCE removed $\cdot$ hr$^{-1}$ $\cdot$ g dry cells$^{-1}$ |
| 10 | 829 |
| 25 | 1104 |
| 50 | 1194 |

These results and the results of other experiments led to the conclusion that the $K_s$ for TCE oxidation is approximately 5 $\mu$M.

Example IX

Degradation of TCE at Various Initial Concentrations

The cell mass of the continuous culture described in Example II was grown to 0.64 g cells.l$^{-1}$. A TCE no head space degradation assay using the procedure described in Example III was performed using these cells. The results are shown below in Table IX.

TABLE IX

| TCE Degradation at Various Initial TCE Concentrations | | | |
| --- | --- | --- | --- |
| Concentration of TCE, $\mu$m | Micromoles TCE removed, $\mu$moles/min. | | |
| | 5–10 min. | 10–15 min. | 10–25 min. |
| 40 | 2.96 | | |
| 80 | 5.69 | 3.03 | |
| 320 | 15.54 | 10.2 | |
| 640 | | | 10.48 |

Example X

Degradation of TCE by Purified Methane Monooxygenase

Radiolabelled TCE was employed in order to demonstrate the oxidation of TCE to products upon incubation with soluble methane monooxygenase in the presence of reduced nicotinamide adenine dinucleotide (NADH). The three components of methane monooxygenase, reductase, component B, and hydroxylase, were purified by the method of Fox and Lipscomb, supra, the disclosure of which is hereby incorporated by reference. All purification procedures were performed at 4° C. The cell paste (100 g) was suspended in 200 ml of 25 mM MOPS, pH 7.0, containing 200 $\mu$ M Fe(NH$_4$)$_2$(SO$_4$)$_2$.6H$_2$O and 2 mM cysteine (Buffer A). The cells were disintegrated by sonication. The sonicated suspension was centrifuged at 48000$\times$g for 60 min. The supernatant was decanted, diluted with an additional 100 ml of buffer A, and adjusted to pH 7.0. The cell free extract was immediately loaded onto a fast flow DEAE Sepharose CL-6B column (40 mm$\times$250 mm) equilibrated with buffer A. The column was then washed with 600 ml of buffer A. All MMO components were completely adsorbed. The MMO components were eluted with a 2000 ml gradient of 0.0 to 0.40M NaCl in buffer A. The hydroxylase eluted at 0.075M NaCl. The two additional fractions required for reconstituted hydroxylase activity, component B and the reductase, eluted at 0.18M NaCl and 0.27M NaCl, respectively. Enzyme incubation mixtures were conducted in sealed 10 ml septum vials, each vial containing the ingredients shown in Table X, below:

TABLE X

| Enzyme Incubation Mixture Components | |
| --- | --- |
| Ingredient | Amount/ Concentration |
| 3-[N-morpholino]propanesulfonic acid (MOPS) buffer[1] at pH 7.5 | 1.5 ml/ 25 mM |
| NADH[2] | 0.1 mM |
| Reductase[3] | 110 $\mu$g |
| Component B | 13 $\mu$g |
| Hydroxylase | 250 $\mu$g |

[1]Sigma Chemical Company, St. Louis, Missouri.
[2]Nicotinamide adenine dinucleotide, reduced form, Sigma Chemical Company, St. Louis, Missouri.
[3]Reductase, component B, and hydroxylase are the three components of methane monooxygenase identified by Fox and Lipscomb, supra.

105 nmol of uniformly labelled $^{14}$C-TCE was added to each vial by injection through the rubber septum above the reaction mixture until a final TCE concentration of 70 $\mu$M was reached. The reaction was allowed to proceed for 2 min at 25° C. and then quenched by the addition of sulfuric acid (Sigma Chemical Company, St. Louis, Miss.) at pH 2.0.

Following centrifugation to remove precipitated protein, the reaction mixtures were analyzed by high pressure liquid chromatography (HPLC). The HPLC operating parameters employed are shown in Table XI, below:

TABLE XI

| HPLC Operating Parameters | |
|---|---|
| Column: | Aminex HPX-87H HPLC column (Bio-Rad) |
| Mobile phase: | 25% acetonitrile (Sigma Chemical Company, St. Louis, Missouri) in 0.01 N sulfuric acid (Sigma Chemical Company, St. Louis, Missouri) |
| Operating mode: | isocratic |
| Rate: | 0.3 ml per min |
| Peak detection: | Ultraviolet spectroscopy, 210 nm |

This HPLC system resolved authentic standards of various potential organic acid products and trichloroacetaldehyde (chloral). Under the enzyme incubation conditions described, 53% of the TCE was converted to HPLC-detectable products. These products were formic acid, glyoxylic acid, dichloroacetic acid, and chloral.

In addition to the above incubations, control incubations were conducted in which each one of the methane monooxygenase components or NADH were omitted. In all of these control experiments, no products of TCE oxidation were detectable.

Thus, this experiment demonstrated that TCE oxidation is catalyzed by the three-component methane monooxygenase enzyme system in the presence of NADH.

The invention has been described with reference to various specific and preferred embodiments and techniques. However, it should be understood that many variations and modifications may be made while remaining within the spirit and scope of the invention.

What is claimed is:

1. A method of degrading a halogenated aliphatic hydrocarbon compound, said method comprising:
    (a) culturing a methane-oxidizing bacterium under continuous culture conditions comprising exposing said bacterium to a continuous-flow gas mixture comprising air and methane in a ratio of about 25:1–1:20, respectively, the continuously cultured methane-oxidizing bacterium producing a soluble methane monooxygenase in an amount from about 5–30% of the weight of dry bacterium cells;
    (b) separating said soluble methane monooxygenase from the continuously cultured methane-oxidizing bacterium;
    (c) purifying the separated soluble methane monooxygenase to yield purified components comprising reductase, component B, and hydroxylase;
    (d) adding each of said purified components to an aqueous mixture of said halogenated aliphatic hydrocarbon compound to form a second mixture; the amount of each of said purified components, when combined with the other two components in said second mixture, being effective to completely degrade said halogenated aliphatic hydrocarbon compound; and
    (e) reacting said second mixture under conditions and for a period of time sufficient for said purified components to completely degrade said halogenated aliphatic hydrocarbon compound.

2. The method of claim 1 wherein said gas mixture comprises air and methane in a ratio of about 10:1–1:2, respectively.

3. The method of claim 2 wherein said gas mixture comprises air and methane in a ratio of about 2.1:1.

4. The method of claim 1 wherein said bacterium is a member of the genus Methylosinus.

5. The method of claim 4 wherein said bacterium is *Methylosinus trichosporium* OB3b.

6. The method of claim 1 wherein said purified components reductase, component B, and hydroxylase are added to said aqueous slurry in a ratio of about 110:13:250, by weight, respectively.

7. The method of claim 1 wherein said halogenated aliphatic hydrocarbon compound is trichloroethylene.

* * * * *

UNITED STATES PATENT AND TRADEMARK OFFICE
CERTIFICATE OF CORRECTION

PATENT NO. : 5,441,887

DATED : August 15, 1995

INVENTOR(S) : Richard S. Hanson et al

It is certified that error appears in the above-indentified patent and that said Letters Patent is hereby corrected as shown below:

Col. 3, lines 16-17, ' Supra" should be --supra--

Col. 5, line 54, "Methylssinus" should be --Methylosinus--

Col. 6, line 11, "OB3b" should be --OB3b--

Col. 7, line 10, "Microlial" should be --Microbial--

Col. 7, line 10, "Whittenburg" should be --Whittenbury--

Col. 7, line 26, "1000-9000 moles" should be --1,000-9,000 $\mu$moles--

Col. 7, lines 28-29, "2000-4000 moles" should be --2,000-4,000 $\mu$moles--

Col. 8, line 7, "77:361" should be --177:361--

Col. 8, line 61, "Components" should be --components--

Col. 9, line 52, "chemestat" should be --chemostat--

Col. 10, line 65, after "at" insert --the--

Col. 11, line 56, "uof" should be --$\mu$1 of--

UNITED STATES PATENT AND TRADEMARK OFFICE
CERTIFICATE OF CORRECTION

PATENT NO. : 5,441,887

DATED : August 15, 1995

INVENTOR(S) : Richard S. Hanson et al

It is certified that error appears in the above-indentified patent and that said Letters Patent is hereby corrected as shown below:

Col. 12, line 31, Second column of Table IV "2,861" should be --2.861--;

Col. 14, line 15, "head space" should be --headspace--

Col. 14, line 44, "moles" should be --$\mu$moles--

Col. 14, line 63, "head space" should be --headspace--

Col. 15, line 44, "head space" should be --headspace--

Col. 15, line 6, "head space" should be --headspace--

Col. 15, line 66, "head space" should be --headspace--

Col. 17, line 12, "isocratic" should be --Isocratic--

Signed and Sealed this

Twenty-ninth Day of April, 1997

*Attest:*

BRUCE LEHMAN

*Attesting Officer*    *Commissioner of Patents and Trademarks*